(12) United States Patent
Dakka et al.

(10) Patent No.: US 8,658,839 B2
(45) Date of Patent: *Feb. 25, 2014

(54) OXIDATION OF HYDROCARBONS

(75) Inventors: Jihad M. Dakka, Whitehouse Station, NJ (US); James C. Vartuli, Bradenton, FL (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 361 days.

This patent is subject to a terminal disclaimer.

(21) Appl. No.: 12/675,342

(22) PCT Filed: Oct. 8, 2008

(86) PCT No.: PCT/US2008/079150
§ 371 (c)(1),
(2), (4) Date: Feb. 25, 2010

(87) PCT Pub. No.: WO2009/058527
PCT Pub. Date: May 7, 2009

(65) Prior Publication Data
US 2010/0222609 A1 Sep. 2, 2010

Related U.S. Application Data

(60) Provisional application No. 60/984,264, filed on Oct. 31, 2007.

(51) Int. Cl.
*C07C 35/08* (2006.01)
*C07D 209/48* (2006.01)

(52) U.S. Cl.
USPC .......................................... 568/836; 548/473

(58) Field of Classification Search
None
See application file for complete search history.

(56) References Cited

U.S. PATENT DOCUMENTS 3,418,256 A 12/1968 Rigney et al.
3,959,381 A 5/1976 Arkell et al.
(Continued)

FOREIGN PATENT DOCUMENTS

DE 2 300 903 1/1973
EP 1 074 536 2/2001
(Continued)

OTHER PUBLICATIONS

Machin translation of JP 11180913.*
(Continued)

*Primary Examiner* — Karl J Puttlitz
(74) *Attorney, Agent, or Firm* — Jamie L. Sullivan; Siwen Chen

(57) ABSTRACT

In a process for oxidizing a hydrocarbon to a corresponding hydroperoxide, alcohol, ketone, carboxylic acid or dicarboxylic acid, the hydrocarbon is contacted with an oxygen-containing gas in the presence of a catalyst comprising a cyclic imide of the general formula (I):

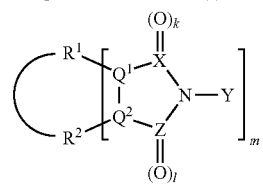

wherein each of $R^1$ and $R^2$ is independently selected from hydrocarbyl and substituted hydrocarbyl radicals having 1 to 20 carbon atoms, or from the groups $SO_3H$, $NH_2$, OH and NO2, or from the atoms H, F, Cl, Br and I provided that $R^1$ and $R^2$ can be linked to one another via a covalent bond; each of $Q^1$ and $Q^2$ is independently selected from C, CH, N and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3, and $R^3$ can be any of the entities listed for $R^1$. The contacting produces an effluent comprising an oxidized hydrocarbon product and unreacted imide catalyst of said formula (I) and the effluent is treated with a solid sorbent to remove at least part of the unreacted imide catalyst and produce a treated effluent comprising said oxidized hydrocarbon product. The organic phase can then be recovered.

21 Claims, 5 Drawing Sheets

(56) References Cited

U.S. PATENT DOCUMENTS

| | | | |
|---|---|---|---|
| 4,136,123 | A | 1/1979 | Hutchings |
| 4,255,592 | A | 3/1981 | Kawai et al. |
| 4,282,383 | A | 8/1981 | Dai et al. |
| 4,450,303 | A | 5/1984 | Drake |
| 5,030,739 | A | 7/1991 | Foricher et al. |
| 5,166,454 | A | 11/1992 | Harandi et al. |
| 5,298,667 | A | 3/1994 | Iwanaga et al. |
| 5,405,814 | A | 4/1995 | Beech, Jr. et al. |
| 5,981,420 | A | 11/1999 | Nakano et al. |
| 6,291,718 | B1 | 9/2001 | Matsui et al. |
| 6,528,658 | B1 | 3/2003 | Miura et al. |
| 6,720,462 | B2 | 4/2004 | Kuhnle et al. |
| 6,852,893 | B2 | 2/2005 | Kuhnle et al. |
| 7,038,089 | B2 * | 5/2006 | De Frutos Escrig et al. .. 568/564 |
| 7,326,815 | B2 | 2/2008 | Dakka et al. |
| 2002/0169331 | A1 * | 11/2002 | Miura et al. ............... 552/1 |
| 2003/0083527 | A1 | 5/2003 | Kuhnle et al. |
| 2004/0014985 | A1 | 1/2004 | Sugahara |
| 2004/0162448 | A1 | 8/2004 | Yang et al. |
| 2004/0236152 | A1 | 11/2004 | Black et al. |
| 2005/0043559 | A1 | 2/2005 | Marhold et al. |
| 2005/0167658 | A1 | 8/2005 | Williams et al. |
| 2007/0265476 | A1 | 11/2007 | Dakka et al. |
| 2008/0269507 | A1 | 10/2008 | Kajikawa et al. |
| 2010/0222609 | A1 | 9/2010 | Dakka et al. |

FOREIGN PATENT DOCUMENTS

| | | | |
|---|---|---|---|
| EP | 1 088 807 | | 4/2001 |
| EP | 1 088 809 | | 4/2001 |
| EP | 1088809 | * | 4/2001 |
| JP | 62-114922 | | 5/1987 |
| JP | 11-180913 | | 7/1999 |
| JP | 11180913 | * | 7/1999 |
| JP | 2001-192354 | | 7/2001 |
| JP | 2004-035460 | | 2/2002 |
| JP | 2002-282698 | | 10/2002 |
| JP | 2002301382 | * | 10/2002 |
| WO | 94/20213 | | 9/1994 |
| WO | 99/47485 | | 9/1999 |
| WO | 9947485 | * | 9/1999 |
| WO | 2006/015826 | | 2/2006 |
| WO | 2008/037435 | | 4/2008 |
| WO | 2009/025939 | | 2/2009 |
| WO | 2010/098916 | | 9/2010 |

OTHER PUBLICATIONS

Ishii et al., Catalyst Today, 117 (2006) 105-113.*
Machine Translation of JP 2002301382.*
"Diatomite" in Kirk-Othmer Encyclopedia of Chemical Technology, Kenneth R. Engh, Published Online: Dec. 4, 2000, Copyright © 2001 by John Wiley & Sons, Inc., pp. 1-9.*
Ishii Y., et al. "*Recent progress in aerobic oxidation of hydrocarbons by N-hydroxyimides*", Catalysis Today, 2006, vol. 117, pp. 105-113.
J. Howard et al., "*Absolute Rate Constants for Hydrocarbon Oxidation. XI. The Reactions of Tertiary Peroxy Radicals*", Canadian Journal of Chemistry, 1968, vol. 47, pp. 2656-2660.
J. Howard et al., "*Absolute Rate Constants for Hydrocarbon Oxidation. VIII. The Reactions of Cumylperoxy Radicals*", Canadian Journal of Chemistry, 1968, vol. 46, pp. 1018-1022.
J. Howard, "*Absolute Rate Constants for Hydrocarbon Autoxidation. XXII. The Autoxidation of Some Vinyl Compounds*", Canadian Journal of Chemistry, 1972, vol. 50, pp. 2298-2304.
J. Howard et al., "*Absolute Rate Constants for Hydrocarbon Autoxidation. XV. The Induced Decomposition of Some T-Hydroperoxides*", Canadian Journal of Chemistry, 1969, vol. 47, pp. 3797-3801.
J. Howard et al., "*Absolute Rate Constants for Hydrocarbon Autoxidation. XIV. Termination Rate Constants for Tertiary Peroxy Radicals*", Canadian Journal of Chemistry, 1969, vol. 47, pp. 3793-3795.
T. Iwahama et al., "*Aerobic Oxidation of Alcohols to Carbonyl Compounds Catalyzed by N-Hydroxyphthalimide (NHPI) Combined with Co (acac)$_3$*", Tetrahedron Letters, 1995, vol. 36, No. 38, pp. 6923-6926.
J. Kochi, "*Chemistry of Alkoxy Radicals: Cleavage Reactions*", Journal of the American Chemical Society, 1962, vol. 84, pp. 1193-1197.
S. Sakaguchi et al., "*Oxidation of Organic Substrates with Molecular Oxygen Catalyzed by Vanadomolybdophosphate ($NPV_6Mo_6$) Combined with N-Hydroxyphthalimide (NHPI)*", Technology Reports of Kansai University, 1996, No. 38, pp. 123-131.
R. Sheldon et al., "*Organocatalytic Oxidations Mediated by Nitroxyl Radicals*", Advanced Synth. Catal., 2004, vol. 346, pp. 1051-1071.
Y. Yen, "*Phenol*", Process Economics Report No. 22B, Stanford Research Institute, 1977, pp. 113-121, 261 and 263.

\* cited by examiner

OXIDATION OF HYDROCARBONS

CROSS-REFERENCE TO RELATED APPLICATIONS

This application is a National Stage Application of International Application No. PCT/US2008/079150 filed Oct. 8, 2008, which claims priority from U.S. Ser. No. 60/984,264 filed Oct. 31, 2007, both of which are incorporated herein by reference.

PRIORITY CLAIM

This application claims the benefit of U.S. Provisional Application Ser. No. 60/984,264 filed Oct. 31, 2007, which is hereby incorporated by reference in its entirety.

FIELD

The present invention relates to a process for oxidizing hydrocarbons and, in particular, alkylaromatic hydrocarbons to produce for example phenol and substituted phenols.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons is used to produce phenol, a precursor in the production of polycarbonates and epoxy resins.

Oxidation of hydrocarbons can be conducted using well-known oxidizing agents, such as $KMnO_4$, $CrO_3$ and $HNO_3$. However, these oxidizing agents have the disadvantage of being relatively expensive, and moreover their use is accompanied by the production of unwanted coupling products which can represent disposal problems and ecological pollution.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autooxidation of hydrocarbons. Thus, for example, the oxidation of cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom from a further hydrocarbon. In addition to metal salts, however, organic molecules can also act as free-radical initiators.

However, it is a disadvantage of these processes that the selectivity decreases very greatly with increasing conversion and therefore the processes must be operated at a very low level of conversion. Thus, for example, the oxidation of cyclohexane to cyclohexanol/cyclohexanone is carried out at a conversion of 10 to 12% so that the selectivity is 80 to 85% ("Industrielle Organische Chemie" [Industrial Organic Chemistry] 1994, 261, VCH-Verlag, D-69451 Weinheim).

An alternative to metal salt catalysts is the use of organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a catalyst, typically a N-hydroxycarbodiimide catalyst, such as N-hydroxyphthalimide (NHPI). The process is conducted at a temperature between 0° C. and 500° C. and a pressure between atmospheric and 100 bar (100 and 10,000 kPa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene and sec-butylbenzene.

U.S. Pat. No. 7,038,089 discloses a process for preparing a hydroperoxide from a hydrocarbon selected from a group consisting of primary hydrocarbons, secondary hydrocarbons and mixtures thereof corresponding to said hydroperoxide which comprises conducting oxidation of said hydrocarbon at a temperature in the range between 130 and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, cymene, ethylbenzene, diisopropylbenzene, cyclohexylbenzene, tetrahydronaphthalene (tetraline), indane, etc.), and the like. The amount of the cyclic imide compound used may be from 0.0001 to 1%, preferably from 0.0005 to 0.5%, by weight based on the reaction mixture, whereas the amount of the alkali metal compound may be from 0.000005 to 0.01%, preferably from 0.00001 to 0.005%, by weight based on the reaction mixture

However, although current work has continued to demonstrate the utility of cyclic imides as hydrocarbon oxidation catalysts, it has also shown that their application in a commercial process requires further investigation. In particular, cyclic imides, such as N-hydroxyphthalimide, are expensive and are readily hydrolyzed under the conditions of the oxidation reaction. Moreover, unreacted imide catalysts and their decomposition products (acids and ethers) can pose significant problems to the downstream reactions, such as hydroperoxide cleavage. Thus the successful application of cyclic imides to the oxidation of hydrocarbons will require treatment of the oxidation effluent to remove unreacted imides and their decomposition products and, if possible, recovery and recycle of the valuable unreacted imides.

According to the invention, it has now been found that unreacted imide catalyst and its decomposition products can be at least partially removed from the effluent of the catalytic oxidation of alkylaromatic compounds by treatment of the effluent with a solid sorbent having basic properties. The unreacted imide is selectively removed from the effluent leaving a product that is essentially free of the imide species. By subsequently washing the adsorbent with a polar solvent, the imide species can be recovered for recycle to the oxidation step.

SUMMARY

In one aspect, the present invention resides in a process for oxidizing a hydrocarbon to a corresponding hydroperoxide, alcohol, ketone, carboxylic acid or dicarboxylic acid, the process comprising (a) contacting a hydrocarbon with an oxygen-containing gas in the presence of a catalyst comprising a cyclic imide of the general formula (I):

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N and $CR^3$;
each of X and Z is independently selected from C, S, $CH_2$, N, P and elements of Group 4 of the Periodic Table;
Y is O or OH;
k is 0, 1, or 2;
l is 0, 1, or 2,
m is 1 to 3; and
$R^3$ can be any of the entities (radicals, groups, or atoms) listed for $R^1$; and
wherein said contacting produces an effluent comprising an oxidized hydrocarbon product and unreacted imide catalyst of said formula (I); and
(b) treating the effluent with a solid sorbent to remove at least part of said unreacted imide catalyst of said formula (I) from said effluent and produce a treated effluent comprising said oxidized hydrocarbon product.

Conveniently, said solid sorbent comprises a metal oxide, a metal carbonate, a hydrogen carbonate, a clayor an ion exchange resin.

Conveniently, said metal oxide has a molar ratio of chemisorption of $CO_2$ per gram of metal oxide to the chemisorption of $NH_3$ per gram of metal oxide greater than 0.5, such as greater than 0.75, for example greater than 1.0.

In one embodiment, the process further comprises recovering the unreacted imide catalyst removed by said solid sorbent and recycling the catalyst to (a). Conveniently, the unreacted imide catalyst is recovered from said solid sorbent by washing the solid sorbent with a polar solvent.

Conveniently, said hydrocarbon is an alkane or cycloalkane, such as isobutane or cyclohexane.

Alternatively, said hydrocarbon is an alkylaromatic compound of general formula (II):

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group.

Conveniently, said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

Conveniently, said cyclic imide obeys the general formula (III):

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;
each of X and Z is independently selected from C, S, $CH_2$, N, P and an element of Group 4 of the Periodic Table;
Y is O or OH;
k is 0, 1, or 2; and
l is 0, 1, or 2.

In one embodiment, said cyclic imide comprises N-hydroxyphthalimide.

In a further aspect, the present invention resides in a process for producing a phenol, said process comprising:
(a) contacting a reaction medium comprising an alkylaromatic compound of general formula (II):

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, with oxygen in the presence of a catalyst comprising a cyclic imide of the general formula (I):

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N and $CR^3$;

each of X and Z is independently selected from C, S, CH$_2$, N, P and elements of Group 4 of the Periodic Table;
Y is O or OH;
k is 0, 1, or 2;
l is 0, 1, or 2;
m is 1 to 3; and
R$^3$ can be any of the entities (radicals, groups, or atoms) listed for R$^1$;
wherein said contacting produces an effluent comprising unreacted imide catalyst of said formula (I) and a hydroperoxide of general formula (IV):

(IV)

in which R$^4$, R$^5$ and R$^6$ have the same meaning as in formula (II);
(b) treating the effluent with a solid sorbent to remove at least part of said unreacted imide catalyst of said formula (I) from said effluent and produce a treated effluent comprising said hydroperoxide of general formula (IV); and
(c) converting the hydroperoxide of formula (IV) from said organic phase into a phenol and an aldehyde or ketone of the general formula R$^4$COCH$_2$R$^5$ (V), in which R$^4$ and R$^5$ have the same meaning as in formula (II).

Conveniently, said contacting (a) is conducted at a temperature of between about 20° C. and about 150° C., such as between about 70° C. and about 130° C. The pressure at which the contacting (a) is conducted is conveniently between about 15 kPa and about 500 kPa, such as between 100 kPa to about 150 kPa.

DETAILED DESCRIPTION OF THE EMBODIMENTS

The terms "group", "radical", and "substituent" are used interchangeably in this document. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical.

Conveniently, each of R$^1$ and R$^2$ is independently selected from aliphatic alkoxy or aromatic alkoxy radicals, carboxy radicals, alkoxy-carbonyl radicals and hydrocarbon radicals, each of which radicals has H$_0$20 carbon atoms.

The present invention provides a process for oxidizing a hydrocarbon to at least one of the corresponding hydroperoxide, alcohol, ketone, carboxylic acid or dicarboxylic acid. The process comprises contacting a reaction medium comprising a hydrocarbon with an oxygen-containing gas in the presence of a catalyst comprising a cyclic imide of the general formula (I):

(I)

wherein each of R$^1$ and R$^2$ is independently selected from hydrocarbyl and substituted hydrocarbyl radicals having 1 to 20 carbon atoms, or the groups SO$_3$H, NH$_2$, OH and NO$_2$, or the atoms H, F, Cl, Br and I, provided that R$^1$ and R$^2$ can be linked to one another via a covalent bond; each of Q$^1$ and Q$^2$ is independently selected from C, CH, N and CR$^3$; each of X and Z is independently selected from C, S, CH$_2$, N, P and elements of Group 4 of the Periodic Table; Y is O or OH; k is 0, 1, or 2; l is 0, 1, or 2; m is 1 to 3; and R$^3$ can be any of the entities (radicals, groups, or atoms) listed for R$^1$. As used herein, the new numbering scheme for the Periodic Table Groups are employed as disclosed in Chemical and Engineering News, 63(5), 27 (1985).

The contacting produces an effluent comprising the desired oxidized hydrocarbon product together with unreacted imide catalyst of said formula (I). The effluent is then treated, before or after concentration of the oxidized hydrocarbon product, with solid sorbent so as to remove at least part, and typically to remove substantially all, of said unreacted imide catalyst from the effluent and produce a treated effluent comprising the oxidized hydrocarbon product. The oxidized hydrocarbon product can then be recovered for further processing.

By washing the imide-loaded solid sorbent with a polar solvent, such as ethanol, the unreacted imide catalyst can be recovered for possible recycle to the oxidation step.

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexyl hydroperoxide, cyclohexanol and cyclohexanone and the selective oxidation to the corresponding hydroperoxides of alkylaromatic compounds of the general formula (II):

(II)

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In an embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^4$ and $R^5$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (II) is sec-butylbenzene and is produced by alkylating benzene with at least one $C_4$ alkylating agent under alkylation conditions and in the presence of a heterogeneous catalyst, such as zeolite Beta or more preferably at least one molecular sieve of the MCM-22 family (as defined below). The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. The contacting pressure may be, for example, from about 100 to about 7000 kPa. The benzene to hydrogen molar ratio in the contacting step is preferably from about 0.01 to about 100. The WHSV during the contacting step is preferably in the range of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is accomplished by contacting the hydrocarbon substrate with an oxygen-containing gas in the presence of a catalyst comprising a cyclic imide of the general formula (I):

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I, provided that $R^1$ and $R^2$ can be linked to one another via a covalent bond; each of $Q^1$ and $Q^2$ is independently selected from C, CH, N and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3, and $R^3$ can be any of the entities (radicals, groups, or atoms) listed for $R^1$. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula (III)

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide.

The conditions used to effect the oxidation step vary significantly with the type of hydrocarbon substrate to be oxidized, but generally suitable conditions include a temperature of between about 20° C. and about 150° C., such as between about 70° C. and about 130° C. The oxidation step is preferably carried out at a pressure between about 15 kPa and about 500 kPa, such as between 15 kPa to about 150 kPa.

Treatment of Oxidation Effluent

Depending on the nature of the hydrocarbon substrate, the product of the oxidation step may include one or more of a hydroperoxide, alcohol, ketone, carboxylic acid or dicarboxylic acid of the corresponding hydrocarbon. In addition, however, the effluent from the oxidation process may contain unreacted cyclic imide catalyst in addition to the desired hydrocarbon oxidation product. Thus, according to the present process, the oxidation effluent is treated with a solid sorbent, which is effective to remove some or substantially all of the unreacted imide catalyst, so as to produce a treated effluent which is rich in said oxidized hydrocarbon product and which contains a reduced or zero level of cyclic imide. Preferably, the sorption process is conducted so as to reduce the level of the imide in the organic phase to less than 100 ppm, such as less than 50 ppm, for example less than 10 ppm, of the organic phase. This is desirable not only because the imide is expensive but also because it can have deleterious effects on downstream operations and separations such as hydroperoxide cleavage.

Suitable solid sorbents are those having basic properties, including metal carbonates and/or hydrogen carbonates, which may be provided on a porous support, clays, ion exchange resins and metal oxides, particularly mixed metal oxides.

Metal oxides having sufficient basic properties to be effective sorbents in the present process may be determined by the molar ratio of chemisorption of $CO_2$ and $NH_3$ over these metal oxide materials. $CO_2$, a mild acid, is used to titrate the basic sites present on the metal oxide being tested. Likewise, $NH_3$, a strong base, is titrated to indicate the acidic sites on the material. Many factors determine the actual amount of chemisorption such as surface area of the material (often significantly affected by the metal oxide preparation method), the temperature at which the chemisorption is tested, and the pressure at which the chemisorption is tested. For the present purposes, a "basic" oxide is defined as an oxide having a molar ratio of chemisorption of $CO_2$ per gram of metal oxide to the chemisorption of $NH_3$ per gram of metal oxide greater than 0.5, typically greater than 0.75, and especially greater than 1.0, when tested as described below.

Testing to determine the molar ratio of chemisorption of $CO_2$ per gram of metal oxide to the chemisorption of $NH_3$ per gram of metal oxide is conducted using a Mettler TGA/SDTA 851 thermogravimetric analysis system at ambient pressure. The metal oxide sample is calcined in flowing air to about 500° C. (except as noted in Table 1) for about three hours, at least until a constant sample weight is obtained. The temperature of the sample is then reduced in flowing air (helium could also be used) to the desired temperature of chemisorption. Next, the sample is allowed to equilibrate at the desired temperature in flowing helium and weighed. Chemisorption of carbon dioxide is measured at 100° C., and chemisorption of ammonia was measured at 250° C. After being weighed, the sample is subjected to a number of pulses (about 12 seconds/pulse) of a gaseous mixture containing helium and either carbon dioxide or ammonia until a constant weight was obtained. The gas mixture contains about 10 weight percent carbon dioxide or ammonia with the remainder being helium. After each pulse of the gas mixture being tested, the metal oxide sample is flushed with flowing helium for about 3 minutes. About 20 separate pulses of the gas mixture is used in each test. The increase in weight of the sample in terms of mg/g metal oxide based on the metal oxide sample weight after calcination is used to determine the moles of $CO_2$ or $NH_3$ adsorbed per gram of metal oxide.

Molar ratios of chemisorption of $CO_2$ to the chemisorption of $NH_3$ per gram of sorbate for some metal oxide species including some of the materials tested in the Examples are shown in Table 1.

TABLE 1

| Material Tested | Calcination Temperature, ° C. | $CO_2/NH_3$ Chemisorption Molar Ratio |
|---|---|---|
| $TiO_2$ | 700 | 0.33 |
| $W/ZrO_2$ | 800 | 0.07 |
| $La_2O_3$ | 700 | 0.86 |
| $La/SiO_2$ | 500 | 0.92 |
| $AlPO_x$ | 500 | 0.75 |
| $NdAlPO_x$ | 500 | 1.04 |
| $YAlPO_x$ | 500 | 0.86 |
| $PrAlPO_x$ | 500 | 1.05 |
| MgO | 700 | 11.47 |
| $Y_2O_3$ | 700 | 14.95 |

Metal oxides suitable for use as solid sorbents in the present process include oxides and mixed oxides of metals of Group 2, Group 3, Group 4, Lanthanide Series, or Actinide Series of the Periodic Table. In one embodiment, the sorbent comprises two or more metal oxides, preferably one Group 4 metal oxide and one or more selected from Group 2, Group 3, Lanthanide Series, and Actinide Series metal oxides. The oxides can be prepared using a variety of methods, although generally are prepared by conversion of a suitable precursor by precipitation from solution and/or calcination. Suitable precursors include metal salts, such as halides, sulfates, phosphates, halides, nitrates, oxychlorides, alkoxides and acetates.

In one embodiment, the metal oxide is produced by first preparing a liquid solution comprising a salt of the metal in a solvent, such as water. The resultant solution is then subjected to conditions sufficient to cause precipitation of the solid oxide material, such as by the addition of a precipitating reagent, typically a base such as sodium hydroxide or ammonium hydroxide. The liquid solution is generally maintained at a temperature at or below 200° C. during the precipitation, for example in the range of from about 0° C. to about 200° C., such as from about 20° C. to about 100° C. The resulting gel is preferably then hydrothermally treated at a temperature of at least 80° C., preferably at least 100° C., for up to 10 days, such as up to 5 days, for example up to 3 days. The resulting material is then recovered, for example by filtration or centrifugation, washed, and dried. The resulting particulate material is typically then calcined, normally in an oxidizing atmosphere, at a temperature of at least 400° C., such as from about 400° C. to about 800° C., for up to 48 hours, such as for about 0.5 hours to about 24 hours, for example for about 1 hour to about 10 hours.

When two or more metal oxides are used, they may either be co-precipitated or precipitated separately and combined with each other at any later stage of processing including as calcined solid particles.

Suitable ion exchange resins for use as the solid sorbent include those resins conventionally employed for removing acidic or basic species, such as Amberlyst exchange resins.

The conditions used in the cyclic imide sorption step are not closely controlled but generally include a temperature of about 10° C. to about 130° C., such as about 20° C. to about 80° C. The time of sorption may be, for example, from about 1 minute to about 30 minutes, such as about 5 minutes to about 10 minutes.

After removal by the solid sorbent, the unreacted cyclic imide can readily be recovered by washing the sorbent with a polar solvent, for example with ethanol or acetone. The recovered imide can then be recycled to the oxidation step, with or without prior removal of the ethanol, since it is found that the presence of ethanol with the imide does not adversely affect the oxidation activity or selectivity of the catalyst (see FIGS. 3 and 4).

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

For example, when the hydrocarbon substrate is isobutane, the oxidation product comprises tertiary butyl hydroperoxide (which is useful as an oxidizing agent e.g., for olefin epoxidation) and tertiary butanol (which is useful as a gasoline additive).

When the hydrocarbon substrate is cyclohexane, the oxidation product comprises cyclohexyl hydroperoxide, cyclohexanol and cyclohexanone. Cyclohexyl hydroperoxide is readily decomposed to additional cyclohexanol and cyclohexanone, either thermally or with the assistance of a catalyst.

Cyclohexanol can be oxidized with aqueous nitric acid to produce adipic acid, which is a precursor in the synthesis of Nylon 6,6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (II), the product of the oxidation reaction includes a hydroperoxide of general formula (IV):

(IV)

in which $R^4$, $R^5$ and $R^6$ have the same meaning as in formula (II). Preferably, the hydroperoxide is sec-butylbenzene hydroperoxide or cyclohexylbenzene hydroperoxide. This hydroperoxide can then be converted by acid cleavage to phenol or a substituted phenol and an aldehyde or ketone of the general formula $R^4COCH_2R^5$ (V), in which $R^4$ and $R^5$ have the same meaning as in formula (II). Phenol can of course be reacted with acetone to produce bisphenol A, a precursor in the production of polycarbonates and epoxy resins.

The hydroperoxide cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the following non-limiting Examples.

Example 1

Preparation of Metal Oxide Sorbents (a) 5% $La/ZrO_2$

A solution was prepared consisting of 7.79 grams of lanthanum nitrate hexahydrate and 30 grams of deionized (DI) water. This solution was slowly added to 61.3 grams of the zirconia prepared in preparation (d) described hereinafter. The product was dried overnight at 80° C. and then calcined in air at 700° C. for 3 hours.

(b) 5% Y/Al$_2$O$_3$

A solution was prepared consisting of 4.3 grams of yttrium nitrate hexahydrate and 30 grams of DI water. This solution was slowly added to 28.65 grams of alumina The product was dried overnight at 80° C. and then calcined in air at 700° C. for 3 hours.

(c) 5% La/SiO$_2$

A solution was prepared consisting of 7.79 grams of lanthanum nitrate hexahydrate and 30 grams of DI water. This solution was slowly added to 56 grams of silica. The product was dried overnight at 80° C. and then calcined in air at 500° C. for 3 hours.

(d) ZrO/O$_2$ 150 grams of ZrO(Cl)$_2$.xH$_2$O was dissolved with stirring in 0.5 liters of distilled water. Another solution containing 50 grams of concentrated NH$_4$OH and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(e) 5% La/Al$_2$O$_3$

A solution was prepared consisting of 3.9 grams of lanthanum nitrate hexahydrate and 30 grams of DI water. This solution was slowly added to 28.65 grams of alumina The product was dried overnight at 80° C. and then calcined in air at 700° C. for 3 hours.

(f) La$_2$O$_3$ 100 grams of La(NO$_3$)$_3$.xH$_2$O was dissolved with stirring in 0.5 liters of distilled water. Another solution containing 20 grams of concentrated NH$_4$OH and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(g) Y$_2$O$_3$ 100 grams of Y(NO$_3$)$_3$.6H$_2$O was dissolved with stirring in 0.75 liters of distilled water. Another solution containing 50 grams of concentrated NH$_4$OH and 0.75 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(h) Nd$_2$O$_3$ 100 grams of Nd(NO$_3$)$_3$.6H$_2$O was dissolved with stirring in 0.5 liters of distilled water. Another solution containing 20 grams of concentrated NH$_4$OH and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(i) Pr$_2$O$_3$ 100 grams of Pr(NO$_3$)$_3$.6H$_2$O was dissolved with stirring in 0.5 liters of distilled water. Another solution containing 20 grams of concentrated NH$_4$OH and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(j) CeO$_2$ 100 grams of Ce(NO$_3$)$_3$.6H$_2$O was dissolved with stirring in 0.75 liters of distilled water. Another solution containing 30 grams of concentrated NH$_4$OH and 0.75 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(k) Sm$_2$O$_3$ 100 grams of Sm(NO$_3$)$_3$.6H$_2$O was dissolved with stirring in 0.5 liters of distilled water. Another solution containing 20 grams of concentrated NH$_4$OH and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(l) 95% Y$_2$O$_3$/5% ZrO$_2$ 150 grams of Y(NO$_3$)$_3$.6H$_2$O and 8.75 grams of ZrO(NO$_3$)$_2$.xH$_2$O were dissolved with stirring in 0.75 liters of distilled water. Another solution containing 100 grams of concentrated NH$_4$OH and 0.75 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(m) 75% Y$_2$O$_3$/25% ZrO$_2$ 150 grams of Y(NO$_3$)$_3$.6H$_2$O and 55.4 grams of ZrO(NO$_3$)$_2$.xH$_2$O were dissolved with stirring in 0.75 liters of distilled water. Another solution containing 100 grams of concentrated NH$_4$OH and 0.75 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(n) $TiO_2$ 150 grams of $TiOSO_4 \cdot H_2SO_4 H_2O$ was dissolved with stirring in 0.5 liters of distilled water. Another solution containing 50 grams of concentrated $NH_4OH$ and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(o) MgO 200 grams of $Mg(NO_3)_2 \cdot 6H_2O$ was dissolved with stirring in 0.5 liters of distilled water. Another solution containing 50 grams of concentrated $NH_4OH$ and 0.5 liters of distilled water was prepared. These two solutions were combined at the rate of 50 ml/min using nozzle mixing. The pH of the final composition was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 700° C. in flowing air for 3 hours to produce an active oxide material.

(p) $SiO_2$ 175 grams of $NaSiO_3$ was dissolved with stirring in 1.6 liters of distilled water. The pH of solution was adjusted to approximately 8 by the addition of 50% sulfuric acid. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(q) 75% $SiO_2$/25% $Al_2O_3$ 132 grams of $NaSiO_3$ was dissolved with stirring in 0.8 liters of distilled water. Another solution consisting of 73 grams of $Al_2(SO_4)_3 \cdot 14H_2O$ and 0.8 liters of deionized $H_2O$ was prepared. The two solutions were combined slowly with stirring. The pH of solution was adjusted to approximately 8 by the addition of 50% sulfuric acid. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(r) 50% $SiO_2$/50% $Al_2O_3$ 88 grams of $NaSiO_3$ was dissolved with stirring in 0.8 liters of distilled water. Another solution consisting of 145 grams of $Al_2(SO_4)_3 \cdot 14H_2O$ and 0.8 liters of deionized $H_2O$ was prepared. The two solutions were combined slowly with stirring. The pH of solution was adjusted to approximately 8 by the addition of 50% sulfuric acid or concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(s) 25% $SiO_2$/75% $Al_2O_3$ 44 grams of $NaSiO_3$ was dissolved with stirring in 0.8 liters of distilled water. Another solution consisting of 218 grams of $Al_2(SO_4)_3 \cdot 14H_2O$ and 0.8 liters of deionized $H_2O$ was prepared. The two solutions were combined slowly with stirring. The pH of solution was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(t) 13% $SiO_2$/87% $Al_2O_3$ 22 grams of $NaSiO_3$ was dissolved with stirring in 0.8 liters of distilled water. Another solution consisting of 253 grams of $Al_2(SO_4)_3 \cdot 14H_2O$ and 0.8 liters of deionized $H_2O$ was prepared. The two solutions were combined slowly with stirring. The pH of solution was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(u) $Al_2O_3$

A solution consisting of 290 grams of $Al_2(SO_4)_3 \cdot 14H_2O$ and 1.6 liters of DI water was prepared. The pH of solution was adjusted to approximately 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this product was calcined to 500° C. in flowing air for 3 hours to produce an active oxide material.

(v) 5% La on Silica Extrudate

A solution was prepared consisting of 7.79 grams of lanthanum nitrate hexahydrate and 30 grams of DI water. This solution was slowly added to 56 grams of silica extrudate. The product was dried overnight at 80° C. and was then calcined in air at 500° C. for 3 hours.

(w) $La/SiO_2$

A solution was prepared by mixing 1000 grams of water and 310 grams of a TMAsilicate (tetramethylammonium silicate) solution containing 10% $SiO_2$ by weight. Another solution was prepared containing 1300 grams of water and 14 grams of lanthanum nitrate hexahydrate. These two solutions were combined with stirring. The pH of the product was adjusted to 9 with the addition of concentrated sulfuric acid. The material was placed in a polypropylene bottle and put in a steam box (100° C.) for 72 hours. The material was then filtered and washed and dried at about 85° C. A portion of the material was air calcined to 500° C. for three hours. The material was then combined with a solution of 1N ammonium nitrate in a ratio of 100 ml of ammonium nitrate solution per 10 grams of silicate material. This mixture was stirred for one hour at room temperature and then filtered. This exchange procedure was repeated a total of four times with fresh ammonium nitrate solution for each time. The material was then washed with deionized water and dried overnight at about 85° C. Finally the material was air calcined at 500° C. for three hours. The chemical analyses were: lanthanum—13.6 weight %, silicon—39.12 weight %. The surface area of the calcined material was 218 $m^2/g$.

(x) $AlPO_x$

A solution was prepared consisting of 500 grams of DI water, 45 grams of concentrated phosphoric acid, and 75 grams of concentrated sulfuric acid. Another solution was prepared consisting of 1600 grams of DI water and 300 grams of sodium aluminate. These two solutions were combined with stirring and the pH was adjusted, if needed, to 9 with the addition of concentrated sulfuric acid. This mixture was then placed in a polypropylene bottle and placed in a steambox at 100° C. for 48 hours. The mixture was then filtered, washed, and dried at 80° C. overnight. The material was then calcined in air at 540° C. for three hours and subsequently ammonium exchanged by slurrying 10 grams of the material per 100 ml of 1N ammonium nitrate solution. This exchange procedure was repeated for a total of 4 times. The exchanged product was then filtered, washed, and then dried overnight at 80° C. Finally, the product was air calcined at 500° C. for three hours.

Example 2

Figure 1:
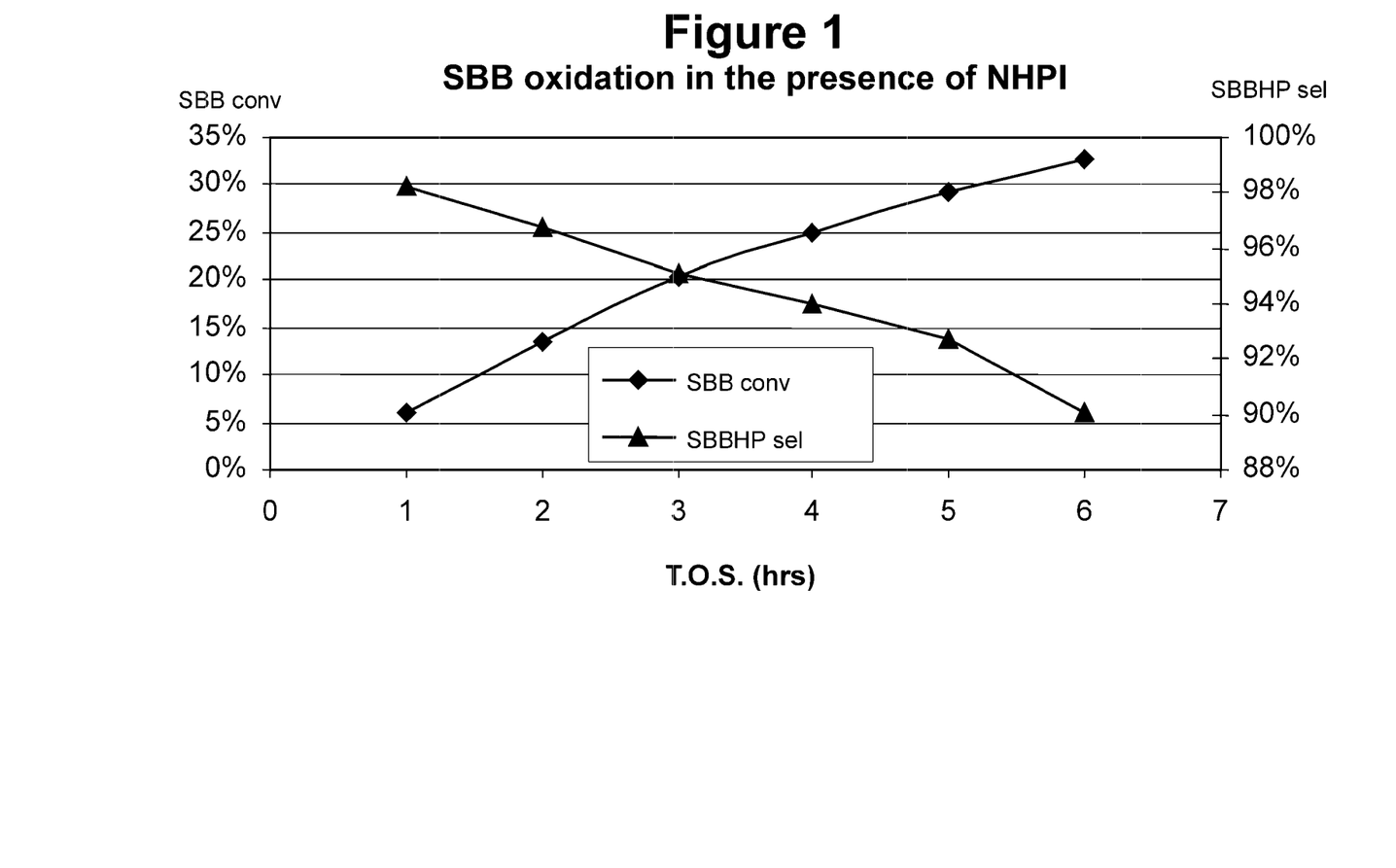
FIG. 1 is a graph plotting conversion and sec-butylbenzene hydroperoxide (SBBHP) selectivity against time on stream (T.O.S.) in the oxidation of sec-butylbenzene (SBB) in the presence of 0.46 wt % NHPI at 690 kPag (100 psig) according to the process of Example 2.

SBB Oxidation in the Presence of NHPI 150 gm of sec-butylbenzene (SBB) supplied by TCI America and 0.69 gm (0.46 wt %) of N-hydroxyphthalimide (NHPI) were weighed into a Parr reactor fitted with a stirrer, thermocouple, gas inlet, sampling port and a condenser containing a Dean Stark trap for water removal. The reactor and contents were stirred at 700 rpm and sparged with nitrogen at a flow rate of 250 cc/minute for 5 minutes. The reactor was then pressurized with nitrogen to 100 psig (790 kPa) while maintained under a nitrogen sparge and was then heated to 115° C. When the reaction temperature was reached, the gas was switched from nitrogen to air and the reactor was sparged with air at 250 cc/minute for 6 hours. Samples were taken hourly and the NHPI and acetic acid concentrations of each sample were measured by gas chromatography. The water analysis was measured by Karl Fisher titration. After 6 hours, the gas was switched back to nitrogen and the heat was turned off. When the reactor had cooled, it was depressurized and the contents removed. The results are shown in FIG. 1.

Example 3

NHPI Removal from the Oxidation Mixture Using Sorbent

Figure 2A:
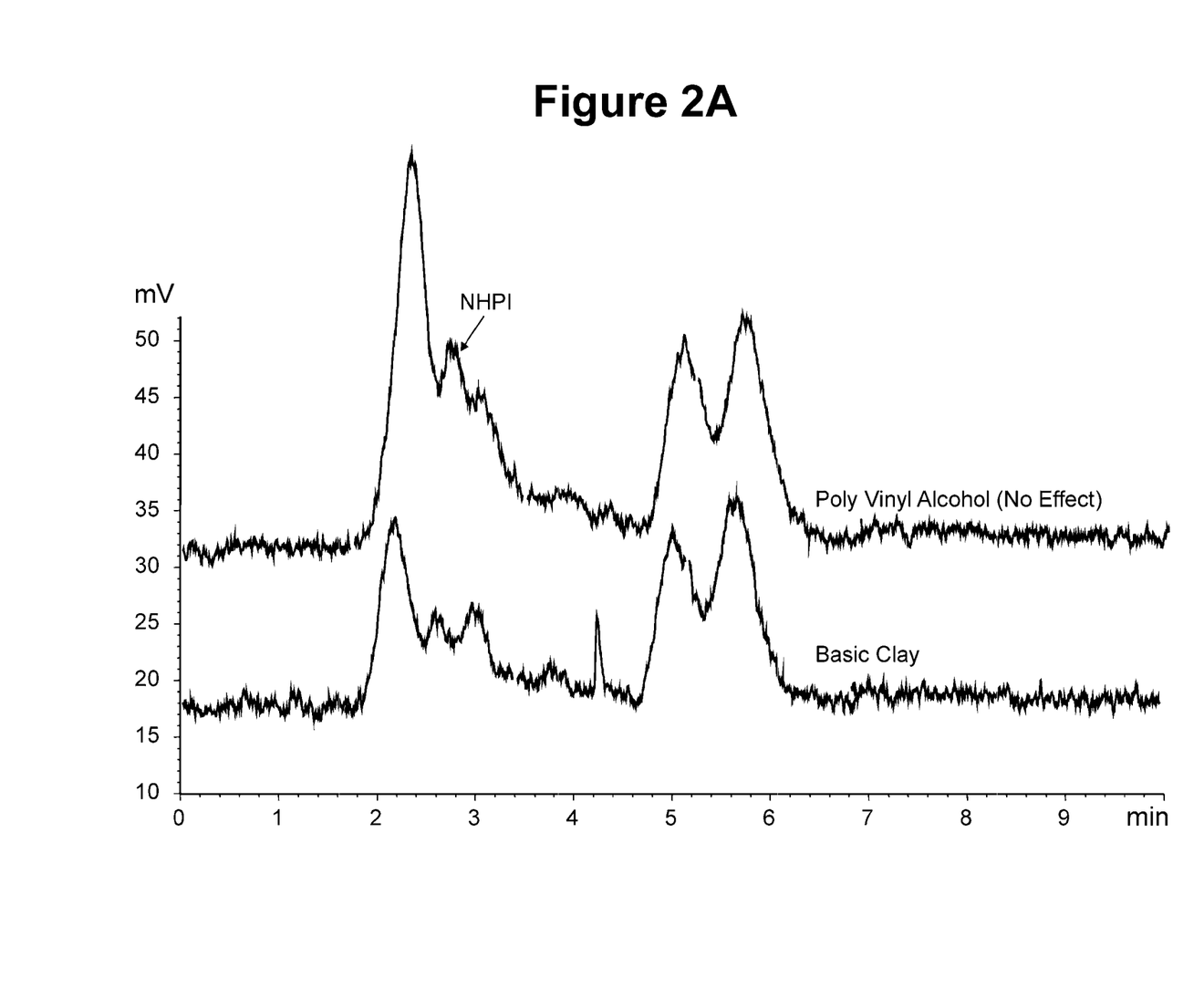
FIGS. 2(a) to (c) are high pressure liquid chromatography (HPLC) spectra of the effluent of the process of Example 2 after extraction of the effluent with various sorbents according to the process of Example 3.
Figure 2B:
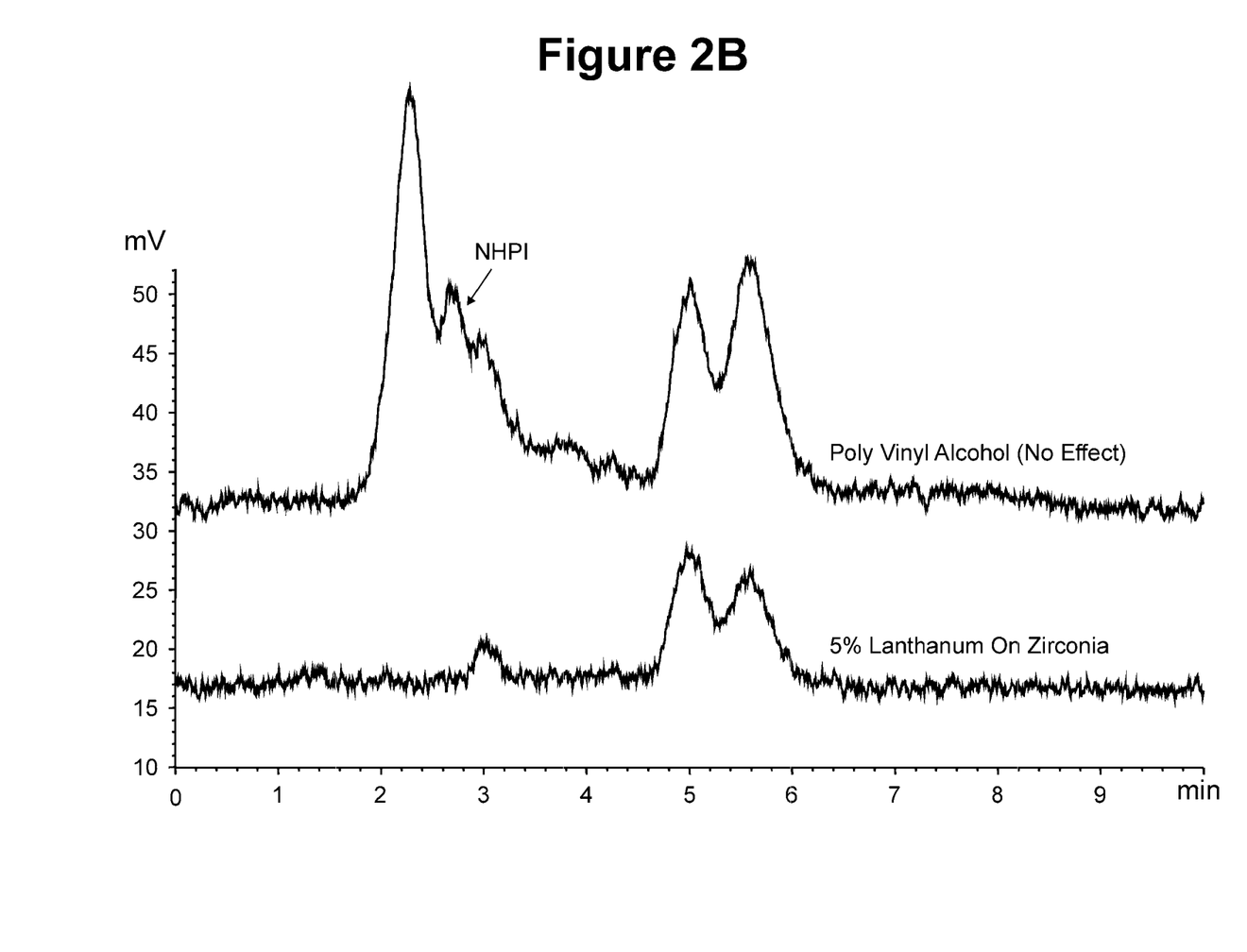
Figure 2C:
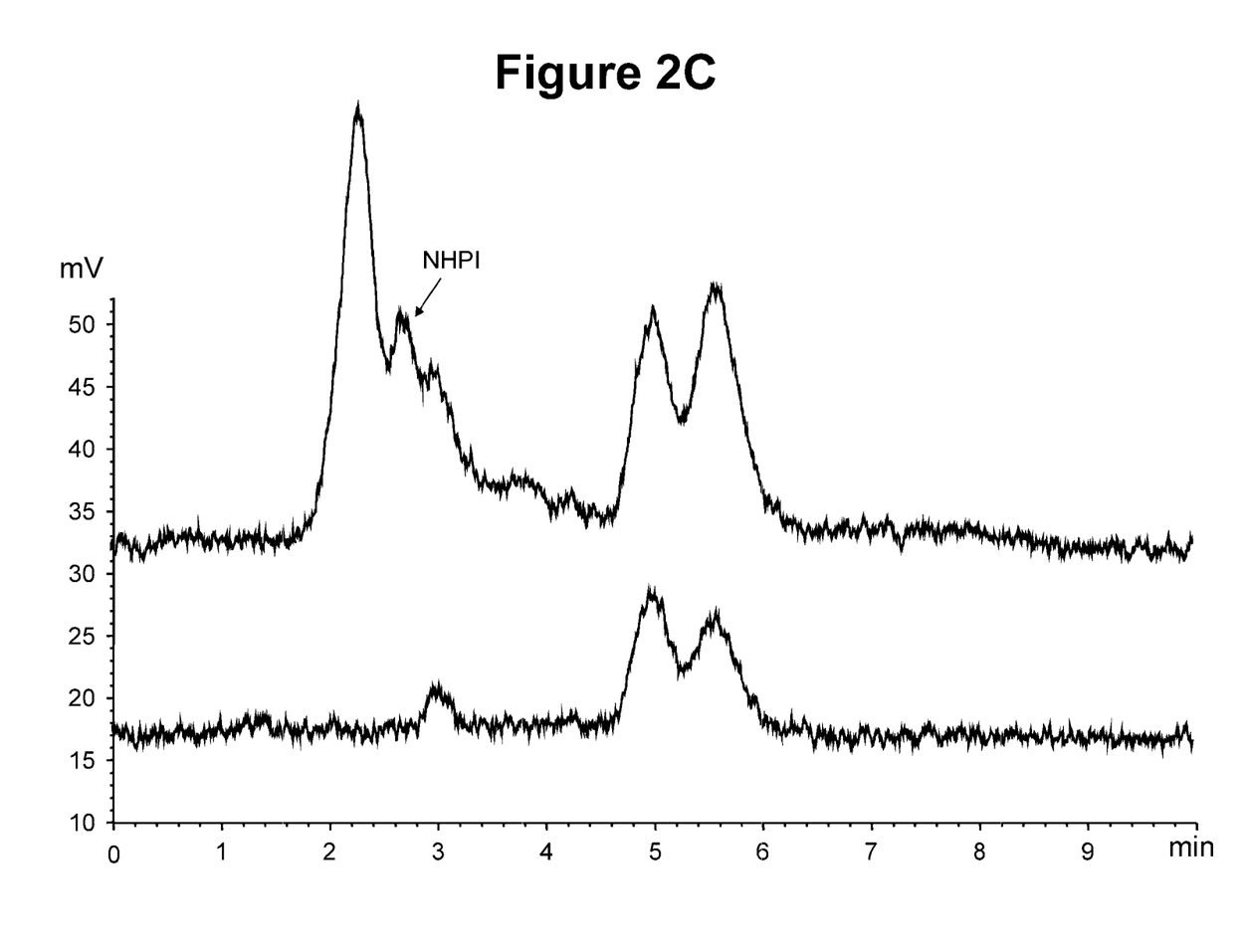

A series of tests were run in each of which a 5 gm sample of the oxidation product from Example 2 was passed through a column which was filled with 1 gm of solid sorbent. Each test was conducted at room temperature (25° C.) under nitrogen flow. The NHPI content was analyzed before and after the sorption treatment, using an HPLC analysis method. The HPLC instrument was attached to two detectors i) UV detector and ii) nitrogen conductive detector. The sorbents employed included polyvinyl alcohol supplied by Aldrich (for comparison purposes only), a basic clay (Natka Kholin, 02-77681) supplied by W. Grace, and the 5% La/ZrO$_2$ and 5% Y/Al$_2$O$_3$ produced in preparations (a) and (b) respectively of Example 1. The results are shown in FIGS. 2(a) to (2(c) and demonstrate that, whereas the polyvinyl alcohol was ineffective in removing the NHPI, the basic clay and the 5% La/ZrO$_2$ and 5% Y/Al$_2$O$_3$ sorbents removed substantially all the NHPI from the oxidation product of Example 2.

Example 4

Figure 3:
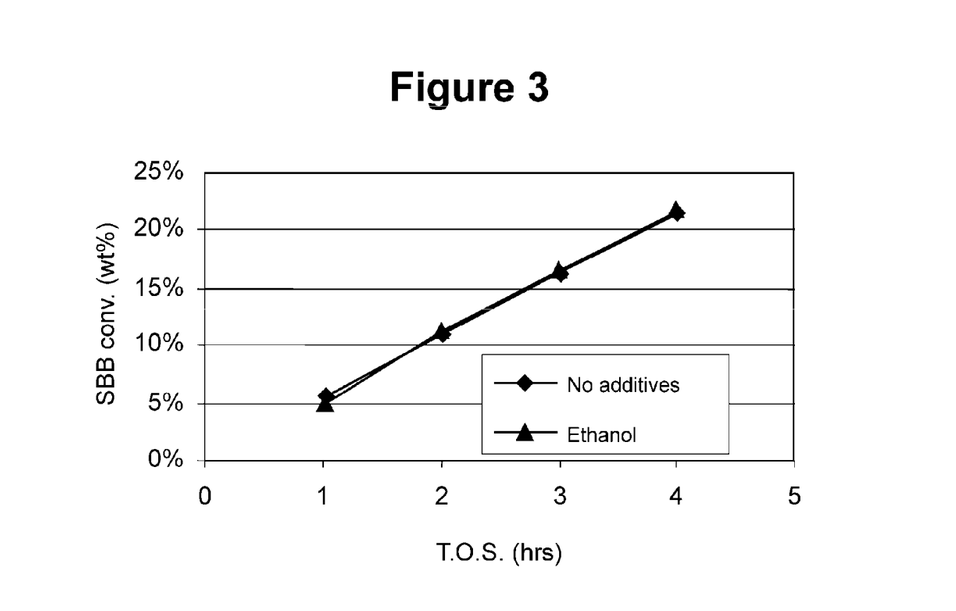
FIG. 3 is a graph plotting sec-butylbenzene (SBB) conversion against time on stream in the oxidation of SBB at atmospheric pressure in the presence of 0.11 wt % NHPI, both with and without the addition of ethanol, according to the process of Example 4.
Figure 4:
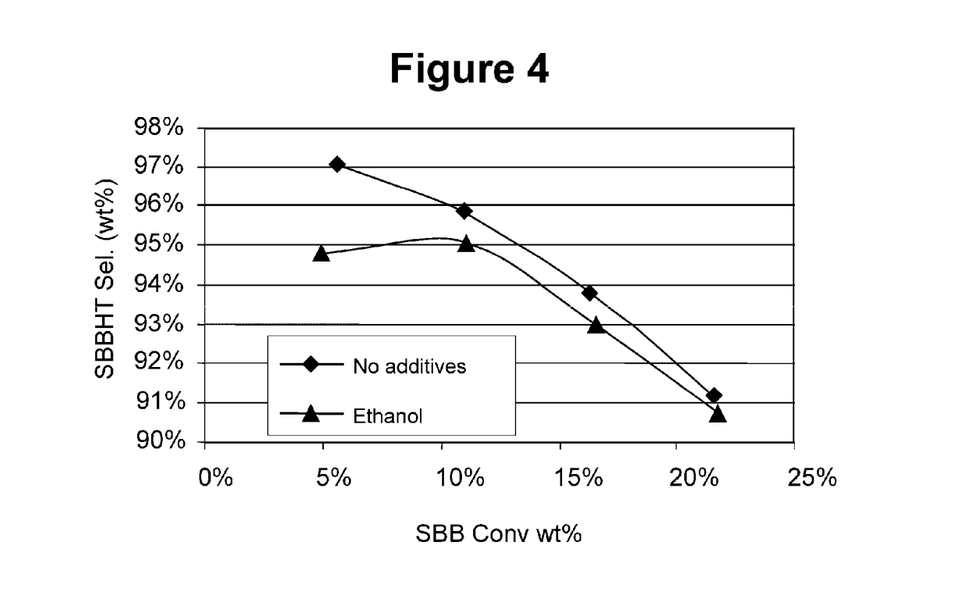
FIG. 4 is a graph plotting sec-butylbenzene hydroperoxide (SBBHP) selectivity against SBB conversion in the process of Example 4.

SBB Oxidation in the Presence of NHPI and Ethanol 150 gm of sec-butylbenzene (SBB) supplied by TCI America and 0.16 gm (0.11 wt %) of N-hydroxyphthalimide (NHPI) and 7.5 gm ethanol were weighed into a Parr reactor fitted with a stirrer, thermocouple, gas inlet, sampling port and a condenser containing a Dean Stark trap for water removal. The reactor and contents were stirred at 1000 rpm and sparged with nitrogen at a flow rate of 250 cc/minute for 5 minutes. The reactor, while maintained under a nitrogen sparge, was then heated to 125° C. When the reaction temperature was reached, the gas was switched from nitrogen to air and the reactor was sparged with air at 250 cc/minute for 4 hours. Samples were taken hourly and the NHPI and acetic acid concentrations of each sample were measured by HPLC and gas chromatography. The water analysis was measured by Karl Fisher titration. After 4 hours, the gas was switched back to nitrogen and the heat was turned off. When the reactor had cooled, it was depressurized and the contents removed. The results are shown in FIGS. 3 and 4 and show that the SBB oxidation with NHPI is substantially unaffected by addition of ethanol. These tests demonstrate that ethanol can be used for recovering NHPI from the absorbent and also for introducing the NHPI to the oxidation reactor.

Example 5

SBB Oxidation in the Presence of NHPI and NHPI Removal from the Oxidation Mixture Using Different Sorbents 150 gm of sec-butylbenzene (SBB) supplied by TCI America and 0.16 gm (0.11 wt %) of N-hydroxyphthalimide (NHPI) were weighed into a Parr reactor fitted with a stirrer, thermocouple, gas inlet, sampling port and a condenser containing a Dean Stark trap for water removal. The reactor and contents were stirred at 1000 rpm and sparged with nitrogen at a flow rate of 250 cc/minute for 5 minutes. The reactor, while maintained under a nitrogen sparge, was then heated to 125° C. When the reaction temperature was reached, the gas was switched from nitrogen to air and the reactor was sparged with air at 250 cc/minute for 4 hours. Samples were taken hourly and the NHPI and acetic acid concentrations of each sample were measured by HPLC and gas chromatography. The water analysis was measured by Karl Fisher titration. After 4 hours, the gas was switched back to nitrogen and the heat was turned off. When the reactor had cooled, it was depressurized and the contents removed.

A series of tests were run in each of which a 5 gm sample of the resultant oxidation product was passed through a column which was filled with various metal oxide species produced in Example 1. The NHPI content (ppm by weight) and the mixture composition were analyzed before and after the sorption treatment, using an HPLC and GC analysis methods. The HPLC instrument was attached to two detectors i) UV detector and ii) nitrogen conductive detector. The results are shown in Table 2.

Example 6

NHPI Removal from the Oxidation Mixture Using Sorbent at 80° C. and Concentrated Hydroperoxide Solution (88 wt %)

A portion of the oxidation product from Example 5 was concentrated by stripping SBB from the product at a temperature of 80° C. and under 13.3 Pa (0.1 mm Hg) vacuum. A series of tests were run in each of which a 5 gm sample of the concentrated product was mixed with various metal oxide species produced in Example 1 and the mixture was heated at 80° C. for 15 minutes. The NHPI content (ppm by weight) and the mixture composition were analyzed before and after the sorption treatment, using an HPLC and GC analysis methods. The HPLC instrument was attached to two detectors i) UV detector and ii) nitrogen conductive detector. The results are shown in Table 3.

TABLE 2

| Sorbent (Example 1 prep.) | NHPI ppm | | Hydroperoxide wt % | |
|---|---|---|---|---|
| | before treatment | after treatment | before treatment | after treatment |
| ZrO2 (d) | 806 | <10 | 19.395 | 19.022 |
| La2O3 (f) | 806 | <10 | 19.395 | 19.243 |
| Y2O3 (g) | 806 | <10 | 19.395 | 18.798 |
| Nd2O3 (h) | 806 | <10 | 19.395 | 19.276 |
| Pr2O3 (i) | 806 | <10 | 19.395 | 19.208 |
| CeO2 (j) | 806 | <10 | 19.395 | 18.645 |
| Sm2O3 (k) | 806 | 270 | 19.395 | 19.597 |
| Y2O3—5% ZrO2 (l) | 806 | <10 | 19.395 | 18.888 |
| Y2O3—25% ZrO2 (m) | 806 | <10 | 19.395 | 18.864 |
| TiO2 (n) | 806 | <10 | 19.395 | 18.935 |
| MgO (o) | 806 | <10 | 19.395 | 19.257 |
| SiO2 (p) | 806 | 121 | 19.395 | 18.863 |
| 75/25 SiO2/Al2O3 (q) | 806 | <10 | 19.395 | 18.629 |
| 50/50 SiO2/Al2O3 (r) | 806 | 18 | 19.395 | 18.878 |
| 25/75 SiO2/Al2O3 (s) | 806 | <10 | 19.395 | 19.059 |
| 13/87 SiO2/Al2O3 (t) | 806 | <10 | 19.395 | 18.906 |
| Al2O3 (u) | 806 | <10 | 19.395 | 18.645 |
| La SiO2 extrudate (v) | 806 | <10 | 19.395 | 19.234 |

TABLE 3

| Sorbent | NHPI ppm | | Hydroperoxide wt % | |
|---|---|---|---|---|
| | before treatment | after treatment | before treatment | after treatment |
| La—SiO2 | 2104 | <10 | 88.123 | 87.914 |
| SiO2 | 2104 | NA | 88.123 | 0.000 |
| La2O3 | 2104 | <10 | 88.123 | 88.201 |
| AlPO | 2104 | <10 | 88.123 | 88.115 |
| Y2O3—5% ZrO2 | 2104 | NA | 88.123 | 0.000 |
| Al2O3 | 2104 | NA | 88.123 | 0.000 |
| CeO2 | 2104 | NA | 88.123 | 0.000 |
| 13/87 SiO2/Al2O3 | 2104 | NA | 88.123 | 0.000 |

Example 7

NHPI Removal from the Oxidation Mixture Using Sorbent Packed Column then Removal of the NHPI from the Column Using Polar Solvent A 0.64 cm (¼ inch) diameter by 15.2 cm (6 inch) long stainless steel column was packed with 3.3 gm La SiO2 extrudate or AlPO samples. The column was heated to 80° C. then 15 gms of the concentrated oxidation product from Example 6 (heated to 80° C.) was pumped through the column at approximately 2 cc/min. Then the column was cooled down to 65° C. and 25 gm ethanol (heated to 65° C.) was pumped through the column. The results show the absorbent removed the NHPI from the concentrated oxidation products at 80° C., and the ethanol removed completely the NHPI from the absorbent. The data showed that the amount of NHPI recovered by ethanol wash is 2144 ppm.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for oxidizing a hydrocarbon to a corresponding hydroperoxide, alcohol, ketone, carboxylic acid or dicarboxylic acid, the process comprising:
   (a) contacting a hydrocarbon with an oxygen-containing gas in the presence of a catalyst comprising a cyclic imide of the general formula (I):

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N and $CR^3$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^3$ can be any of the entities listed for $R^1$; and
wherein said contacting produces an effluent comprising an oxidized hydrocarbon product and unreacted imide catalyst of said formula (I); and
   (b) treating the effluent with a solid sorbent selected from a metal carbonate, a hydrogen carbonate, a basic clay, a metal oxide having a molar ratio of chemisorption of $CO_2$ per gram of metal oxide to the chemisorption of $NH_3$ per gram of metal oxide greater than 0.5, an ion exchange resin for removing acidic species, and mixtures of any two or more thereof, to remove at least part of said unreacted imide catalyst of said formula (I) from said effluent and produce a treated effluent comprising said oxidized hydrocarbon product having a reduced concentration of unreacted imide catalyst compared to the effluent before treatment.

2. The process of claim 1, wherein said cyclic imide obeys the general formula (III):

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$ or from the atoms H, F, Cl, Br and I;

each of X and Z is independently selected from C, S, $CH_2$, N, P and elements of Group 4 of the Periodic Table;
Y is O or OH,
k is 0, 1, or 2, and
l is 0, 1, or 2.

3. The process of claim 1, wherein the cyclic imide is N-hydroxyphthalimide.

4. The process of claim 1, wherein the contacting (a) is conducted at a temperature of between 20° C. and 150° C.

5. The process of claim 4 wherein the temperature is between 70° C. and 130° C.

6. The process of claim 1, wherein contacting (a) is conducted at a pressure between 15 kPa and 500 kPa.

7. The process of claim 6 wherein the pressure is from 15 kPa to 150 kPa.

8. The process of claim 1, wherein the solid sorbent is selected from a metal oxide having a molar ratio of chemisorption of $CO_2$ per gram of metal oxide to the chemisorption of $NH_3$ per gram of metal oxide greater than 0.75.

9. The process of claim 8, wherein the ratio is greater than 1.0.

10. The process of claim 1 and further comprising recovering the unreacted imide catalyst removed by the solid sorbent and recycling the catalyst to (a).

11. The process of claim 10, wherein the unreacted imide catalyst is recovered from the solid sorbent by washing the solid sorbent with a polar solvent.

12. The process of claim 1, wherein the hydrocarbon comprises an alkane or cycloalkane.

13. The process of claim 12, wherein the hydrocarbon comprises isobutane or cyclohexane.

14. The process of claim 13, wherein the hydrocarbon comprises cyclohexane, the oxidized hydrocarbon product comprises cyclohexanol and the process further comprises converting the cyclohexanol to adipic acid.

15. The process of claim 13, wherein the hydrocarbon comprises cyclohexane, the oxidized hydrocarbon product comprises cyclohexanone and the process further comprises converting the cyclohexanone to caprolactam.

16. The process of claim 13, wherein the hydrocarbon comprises iso-butane, the oxidized hydrocarbon product comprises tert-butyl hydroperoxide and the process further comprises using the tert-butyl hydroperoxide as an oxidation catalyst.

17. The process of claim 1, wherein the hydrocarbon comprises an alkylaromatic compound of general formula (II):

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, and wherein the oxidized hydrocarbon product comprises a hydroperoxide of general formula (IV):

(IV)

in which $R^4$, $R^5$ and $R^6$ have the same meaning as in formula (II).

18. The process of claim 17, wherein the alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

19. The process of claim 18, wherein the alkylaromatic compound is sec-butylbenzene or cyclohexylbenzene.

20. The process of claim 1 and further comprising converting the hydroperoxide of formula (IV) into a phenol and an aldehyde or ketone of the general formula $R^4COCH_2R^5$ (V), in which $R^4$ and $R^5$ have the same meaning as in formula (II).

21. The process of claim 20 and further comprising converting the phenol produced into bisphenol.

* * * * *